United States Patent [19]

Mallia et al.

[11] Patent Number: 5,112,952
[45] Date of Patent: May 12, 1992

[54] COMPOSITION AND METHOD FOR ISOLATION AND PURIFICATION OF IMMUNOGLOBULIN M

[75] Inventors: A. Krishna Mallia, Rockford, Ill.; Marten W. Wendt, Perstorp, Sweden

[73] Assignee: Pierce Chemical Company, Rockford, Ill.

[21] Appl. No.: 589,409

[22] Filed: Sep. 28, 1990

[51] Int. Cl.$^5$ .......................... C07K 3/20; C07K 17/10
[52] U.S. Cl. .................................. 530/387.1; 530/402; 530/411; 530/413; 530/813; 530/388.1; 530/863; 530/864
[58] Field of Search ............... 530/413, 411, 813, 387, 530/389, 396, 402

[56] References Cited

PUBLICATIONS

Kozutsimi et al., "Isolation And Characterization Of A Mannan-Binding Protein From Rabbit Serum," *Biochem. Biophys. Res. Comm.*, vol. 95, No. 2, Jul. 31, 1980, pp. 658-664.

Lu et al., "Binding of the Pentamer/Hexamer Forms Of Mannan-Binding Protein . . . ", *J. Immunol.*, vol. 144, No. 6, Mar. 15, 1990, pp. 2287-2294.

Nethery et al, "Single-step purification of immunoglobulin M on Clq-Sepharose," *J. Immunol. Methods*, vol. 126, 1990, pp. 57-60.

Ohto et al., "The Mechanism of Carbohydrate-mediated Complement Activation by the Serum Mannan-binding Protein," *J. Biol. Chem.*, vol. 265, No. 4, Feb. 5, 1990, pp. 1980-1984.

Shibuya et al., "One-Step Purification of Murine IgM . . .", *Arch Biochem, Biophys.*, vol. 267, No. 2, Dec. 1988, pp. 676-680.

*Primary Examiner*—Jeffrey E. Russel

[57] ABSTRACT

Preparation of a composite of mannan binding protein attached to an insoluble, support matrix is accomplished by reacting cyanogen bromide activated beaded agarose with a buffered solution of mannan binding protein isolated from rabbit serum. The composite has utility as an affinity sorbent for IgM when divalent metal ions are incorporated in the binding buffer. The composite does not show cross-reactivity (binding) with immunoglobulins of the G class.

10 Claims, No Drawings

COMPOSITION AND METHOD FOR ISOLATION AND PURIFICATION OF IMMUNOGLOBULIN M

FIELD OF THE INVENTION

This invention pertains to the ability of a known and available mammalian serum protein to form a reversible complex with Immunoglobulin M (IgM) in the presence of calcium ions. More particularly, the invention provides an affinity chromatographic method for the preparative isolation and purification of IgM from a complex biological mixture such as serum in a reliable, specific and efficient manner.

BACKGROUND OF THE INVENTION

Immunoglobulins are high molecular weight proteins which fall into five major classes: IgA, IgD, IgE, IgG and IgM. Collectively, these proteins are commonly referred to as antibodies. Antibodies form, for nearly all higher organisms, the basis of a fundamental immunological defense system against a variety of pathological insults.

A characteristic property of antibodies, regardless of class, is that they function in their defense roles by forming specific complexes with portions of the invading pathogen. This feature of antibodies has been exploited in-vitro for a large variety of analytical testing applications such as Radio Immuno Assay (RIA), and Enzyme Linked Immunoassay (ELISA). In-vivo, the specific binding properties of antibodies has been exploited in a large variety of immuno-therapy and imaging techniques.

The medical and commercial importance of antibodies has resulted in a variety of techniques designed to isolate and purify antibodies of a particular class.

A particularly useful method for IgG isolation involves the use of immobilized Protein-A in an affinity chromatographic format. (U.S. Pat. No. 3,995,018 to Sjoquist). Protein A is a bacterial wall derived protein from *Staphylococcus aureus* or derived more conveniently via recombinant techniques. A deficiency inherent in the use of protein-A for IgG isolation is that preparations are frequently contaminated with antibodies from the IgM and IgA class. Protein G, a bacterial wall protein derived from group *G Streptococci*, has also enjoyed utility as an IgG binding protein and has been shown to show greater specificity toward IgG than does protein A.

Jacalin, an alpha-D-galactose binding lectin extracted from jack-fruit seeds (*Artocarpus integrifolia*) has been reported to possess bio-specific binding properties for human IgA (Kumar, et al., J. Biosci. 4, p 257–261 (1982)). By use of immobilized jacalin, human IgA can be prepared which is free of contaminating IgG or IgM.

Unfortunately, very little has been available to the investigator with which to pursue practical methods for the isolation of IgM. This paucity of methodology is in spite of the fact that IgM is an extremely valuable class of immunoglobulin. For example, with many antigenic challenges, IgM is the only class of antibody produced by the host animal.

Recently, Nethery, et al., in the Journal of Immunological Methods, 126 (1990) p 57–60 described a single-step affinity chromatographic method for purification of IgM based upon a temperature dependant interaction of immobilized protein C1q with IgM. The method for IgM purification based on C1q represents a marked improvement over what has been heretofore described. However, as recognized by Nethery, et al., C1q binds not only to IgM, but also IgG. C1q has been reported to have substantial binding affinity for monomeric IgG based upon observations by Sledge and Bing, J. Biol. Chem. 248, 2818–2823 (1973). The result of binding ability of C1q for IgG is that preparations of IgM based upon a C1q affinity matrix may be adulterated with various and sporadic levels of IgG. Thus, an object of the instant invention is to provide an efficient isolation process which can be used to obtain IgM in substantially pure form uncontaminated by IgG.

SUMMARY OF THE INVENTION

Now in accordance with the instant invention, there is provided an improved method for the rapid and efficient isolation of highly purified IgM from an aqueous sample containing IgM together with various impurities which takes advantage of the specific, calcium ion dependent binding between the readily available, economical serum protein, mannan binding protein (MBP) and IgM. More particularly, the method of the present invention comprises:

a) preparing a composite of a water insoluble particle having attached thereto mannan binding protein; and b) mixing an IgM containing sample together with a divalent metal ion containing buffer with the composite, c) washing the composite containing the bound IgM with an aqueous buffer containing a divalent metal ion to remove unbound impurities and d) releasing the bound, highly purified IgM from the composite and recovering said purified IgM.

The foregoing, if desired, can be reiterated by repeating steps b, c, and d after re-equilibrating the composite with fresh divalent metal containing buffer.

Preferably, the water insoluble particle referred to in step a) above is beaded agarose. It will be recognized by others with ordinary skill in the art of affinity chromatography, that other water insoluble particles or surfaces could also be employed to carry out this invention. In this regard, commercially available, water insoluble particles such as beaded cellulose, fibrous cellulose or synthetic polymer supports such as Trisacryl TM or Fractogel TM are useful for this invention.

The source of mannan binding protein (MBP) used to prepare the composite of this invention is not critical. The preferred source is rabbit serum. Furthermore, the method of attachment of MBP to the water insoluble particle is not considered critical so long as the attachment is reasonably stable (i.e., greater than 98% of attached MBP remains attached during the course of IgM isolation). A chemical method of attachment such as offered by cyanogen bromide activation of the water insoluble particle is the preferred method of attachment.

With respect to choice of divalent metal ion present in the aqueous buffer utilized for binding and washing in b) and c) above, useful ions include calcium, magnesium and zinc with calcium being preferred.

The preferred condition for release of bound, washed IgM from the composite in step d) is to include an agent which will effectively bind any divalent metal ion thereby dissociating the IgM/MBP complex. The preferred reagent for binding divalent metal ion is ethylene diamine tetraacetic acid (EDTA). A less preferred, albeit, useful method of releasing purified IgM in step d)

would involve lowering the pH of the buffer to about 3.0.

Further, in accordance with the present invention are provided composites as described above consisting of water insoluble particles having attached thereto MBP.

DETAILED DESCRIPTION OF THE INVENTION

Both mannan binding protein from serum and C1q are well known and characterized proteins. C1q constitutes a member of the immunological system referred to as "complement". MBP is a protein of unknown biological function which derives its name from the observation that it binds to mannan, a complex carbohydrate produced by a variety of yeast organisms. MBP has an apparent molecular mass of about 650,000 daltons consisting of approximately 18 identical subunits of around 31,000 daltons. Ohta, et al., in the Journal of Biological Chemistry, 265, (1990) p 1980–1984 describe MBP as having a gross structure remarkably homologous with that of C1q which also has 18 polypeptide subunits of 24–28,000 daltons each yielding a combined molecular mass of approximately 460,000 daltons. C1q has been described (Wines, et al., Molecular Immunology, 27 (1990) p 221–226) as "resembling a bunch of tulips, the central fibril and radiating stalks being composed of collagen triple helices and the six globular "flower heads" containing $\beta$-sheet." Although C1q and MBP are structurally similar proteins, the instant invention discloses surprising differences between C1q and MBP with respect to binding conditions, capacity for IgM and specificity for IgM.

MBP is isolated by a known and described method (Y. Kozutsumi, et al., Biochem. Biophys. Res. Comm. (1980) 95, p 658–664) involving the passage of calcium containing buffer mixed with rabbit serum over a chromatographic column containing mannan (ex. *Saccharomyces cerevisiae*) which has been chemically immobilized to an insoluble beaded support. Substances other than MBP are not significantly retained by this column.

EXAMPLE 1

Preparation of Immobilized Mannan 600 ml of Sepharose TM 6B, a brand of beaded agarose manufactured by Pharmacia, is washed on a filter pad with 10 liters of deionized water, transferred to a 2 liter capacity beaker and then suspended in 600 ml of deionized water with the aid of an overhead stirrer. The beaded agarose slurry is activated in a well ventilated area such as a hood by portionwise addition of 120 grams of solid cyanogen bromide over a 20 minute period while simultaneously maintaining the temperature at approximately 20° C. (by addition of ice directly into the stirred slurry) and maintaining the pH of the slurry at approximately 10.5–11.0 by dropwise addition of concentrated sodium hydroxide solution. The CNBr activated agarose beads are washed on a filter pad with 10 liters of ice-cold deionized water and 1 liter of ice-cold 0.1M sodium bicarbonate solution then suction dried on the filter pad. The suction dried, CNBr activated and washed agarose beads are added to a 10.7 grams of yeast mannan (ex *Saccharomyces cerevisiae*) obtained commercially as product number M-7504 from Sigma Chemical Co., St. Louis, Mo. U.S.A. dissolved in 600 ml of 0.1M sodium bicarbonate. The reaction mixture is allowed to stir at room temperature overnight. The next day, the agarose beads now having the yeast mannan chemically bonded to it is filtered on a filter pad, washed with 5 liters of deionized water and then suspended in 1 liter of a 0.1M ethanolamine, pH 9.0 solution for 1 hour at room temperature in order to block remaining active sites on the bead surface. The beads following an additional 5 liter wash on the filter pad with deionized water are ready for use in the isolation of mannan binding protein (MBP).

EXAMPLE 2

Preparation of Mannan Binding Protein (MBP).

The following procedure is conducted at 4° C. 450 ml of mannan-//-Sepharose TM 6B prepared as in example 1, is packed in an appropriately sized chromatographic column and equilibrated by washing with 1.0 liters of LOADING BUFFER (10 mM imidazole+20 mM $CaCl_2$+1.25M NaCl, pH 7.8). 5.5 liters of rabbit serum (trace hemolyzed, non-sterile; obtained commercially from Pel-freez, Rogers, Ark. as product no. 31119-5) is mixed with 5.5 liters of SERUM MIXING BUFFER (20 mM imidazole+40 mM $CaCl_2$+2.5M NaCl, pH 7.8) and centrifuged at 8000 rpm for 20 minutes and passed through a cotton plug. The clarified sample-mixture is pumped or gravity fed through the immobilized mannan column at a rate of approximately 100–200 ml/hr which requires 2–3 days.

After the sample has been loaded through the column, the column is washed, by pumping or gravity feed, a total of 2.6 liters of LOADING BUFFER. Washing is continued until the absorbance at 280 nm of wash effluent is no greater that 0.038 absorbance units. Mannan binding protein is eluted from the washed column by introduction of ELUTING BUFFER (10 mM imidazole+1.25M NaCl+2 mM EDTA, pH 7.8) by gravity feed or pump and collecting fractions exiting the column containing 280 nm absorbing material. A typical result form this procedure yields 400 ml of combined eluent fractions having an absorbance (1 cm) at 280 nm of 0.337. This combined fraction contains MBP and trace amounts of contaminating proteins as determined by SDS gel electrophoresis and is of suitable purity to use in preparation of immobilized MBP.

EXAMPLE 3

Preparation of Immobilized Mannan Binding Protein

The composite of this invention can be prepared as follows: 87 ml of Sepharose TM 2B is washed with 500 ml of water, suction dried and transferred to a 500 ml beaker and suspended in 100 ml of water. The gel is activated with 17.4 gm of CNBr, washed, and suction dried in a manner described in example 1. The suction dried, activated gel is added to the 400 ml of isolated MBP solution prepared in example 2 and stirred overnight at 4 deg. C. The next day, the reaction mixture is filtered and washed with 600 ml of water (water washes are saved to determine the amount of uncoupled MBP remaining in solution). The gel is then suspended in 1.0M ethanolamine, pH 9.0, and left for 90 minutes to block any remaining active sites on the gel surface. The gel is then filtered and washed extensively with water. Analysis of initial washes by 280 nm absorbance indicates that approximately 70% of the MBP initially in the reaction slurry will chemically attached to the activated Sepharose 2B when following this protocol.

EXAMPLE 4

Isolation/Purification of Murine IgM Using Immobilized MBP.

At a temperature of 4° C., MBP-Sepharose 2B (5 ml) as prepared in example 3 was packed into a chromatographic column and washed with 15 ml of LOADING BUFFER (10 mM imidazole+20 mM $CaCl_2$+1.25M NaCl, pH 7.8). Two milliliters of mouse ascites solution which has been previously dialyzed against a solution containing 10 mM imidazole+1.25M NaCl, pH 7.8 was mixed with 2 ml of LOADING BUFFER. The 4 ml sample was shown to contain approximately 5 mg of mouse IgM by an enzyme linked immunoassay technique. The column was washed with a total of 48 ml of LOADING BUFFER. The column was then brought to room temperature and eluted by applying 5 column volumes of ELUTING BUFFER (10 mM imidazole+2 mM EDTA+1.25M NaCl, pH 7.8). Yield of purified mouse IgM from this MBP-Sepharose 2B column chromatography is 1100 micrograms.

EXAMPLE 5

Comparison of Immobilized C1q with Immobilized MBP with Respect to Immunoglobulin G (IgG) Binding This example demonstrates the specificity offered by MBP when compared to C1q.

At a temperature of 4° C., 5.0 ml of MBP-Sepharose 2B as prepared in example 3 and packed in a disposable chromatographic column was equilibrated with three column volumes of LOADING BUFFER (10 mM imidazole+20 mM $CaCl_2$+1.25M NaCl, pH 7.8). A solution containing 10.0 mg of human IgG dissolved in 1.0 ml 0.9% NaCl and 1.0 ml of LOADING BUFFER was applied to the column followed by washing with about five column volumes of LOADING BUFFER. Any bound protein is then eluted at room temperature with about five column volumes of ELUTING BUFFER (10 mM imidazole+2 mM EDTA+1.25M NaCl, pH 7.8). No IgG applied bound to the column as determined by 100% recovery of IgG in the wash volume and the absence of any chromatographic peak during elution conditions.

The same experiment was repeated at a temperature of 4° C. using immobilized C1q on Sepharose 4B prepared by the method described by Nethery, et al. The C1q column was equilibrated with three columns of C1q-BUFFER also described by Nethery (50 mM sodium phosphate+150 mM NaCl+2 mM EDTA+0.02% sodium azide, pH 7.2). The 10 mg of human IgG was dissolved in 1.0 ml of 0.9% NaCl and 1.0 ml of C1q-BUFFER and applied to the column followed by five column volumes of washing with the C1q-BUFFER. Elution was achieved continuing the flow of C1q-BUFFER after equilibrating the system at room temperature. In excess of 10% (1.22 mgs) of the applied IgG bound to the immobilized C1q column which eluted as a discrete peak.

EXAMPLE 6

Effect of Buffer Composition when Utilizing Immobilized C1q or Immobilized MBP for IgM Isolation.

This example demonstrates a divalent metal ion requirement in order for IgM to bind immobilized MBP whereas divalent metal ion is contraindicated for IgM binding to immobilized C1q. This difference in buffer requirements indicates a different binding mechanism for MBP/IgM binding compared to C1q/IgM binding.

The IgM purification examples recited in example 4 were repeated with the substitution of human IgM samples for the murine IgM challenge. Both the immobilized C1q column and the immobilized MBP column demonstrated capacity for the human IgM equivalent in amount and degree as described for mouse IgM when using the buffers and conditions described in example 4. When C1q-BUFFER, which contains no calcium ions, was substituted for LOADING BUFFER, no human IgM bound to the immobilized MBP column. When LOADING BUFFER, which contains 20 mM $CaCl_2$, was substituted for C1q-BUFFER, no human IgM bound to the immobilized C1q column.

We claim:

1. A composite, X—Y, wherein X is a water insoluble particle and Y is the protein, mannan binding protein (MBP) covalently attached to X.

2. The composite according to claim 1 wherein X is beaded agarose.

3. The composite of claim 1 wherein Y is mannan binding protein derived from rabbit serum.

4. The composite of claim 3 wherein X is beaded agarose.

5. A method for isolation and purification of Immunoglobulin M (IgM) from an aqueous sample containing IgM together with various impurities comprising the steps of:
   a) mixing said sample with the composite of claim 1,2,3, or 4 in the presence of a divalent metal ion to effect binding of IgM in the sample to the mannan binding protein (MBP) of the composite;
   b) washing the composite containing the bound IgM with an aqueous buffer thereby removing unbound impurities; and
   c) releasing the IgM from the composite and recovering IgM.

6. The method as claimed in claim 5, wherein the sample contains IgG impurity.

7. The method as claimed in claim 5, wherein the divalent metal ion component of the aqueous buffer is calcium ion.

8. The method as claimed in claim 5, wherein releasing the IgM from the composite is accomplished by washing the composite with an aqueous buffer containing a water soluble calcium chelating reagent.

9. The method as claimed in claim 8, wherein the water soluble calcium chelating reagent is EDTA.

10. The method as claimed in claim 5, wherein the steps of IgM binding, washing and releasing are accomplished in a chromatographic column.

* * * * *